United States Patent [19]

König et al.

[11] Patent Number: 4,711,847
[45] Date of Patent: Dec. 8, 1987

[54] PREPARATION OF SECRETIN

[75] Inventors: Wolfgang König, Hofheim am Taunus; Joachim Engels, Kronberg; Eugen Uhlmann, Königstein; Waldemar Wetekam, Eppstein, all of Fed. Rep. of Germany

[73] Assignee: 501 Hoechst Aktiengesellschaft, Frankfurt am Main, Fed. Rep. of Germany

[21] Appl. No.: 638,789

[22] Filed: Aug. 8, 1984

[30] Foreign Application Priority Data

Aug. 10, 1983 [DE] Fed. Rep. of Germany ....... 3328793

[51] Int. Cl.$^4$ .................. C12P 21/02; C12P 21/06; C12N 15/00; C12N 9/78
[52] U.S. Cl. ........................ 435/70; 435/68; 435/69; 435/71; 435/172.3; 435/227; 435/228; 935/14; 935/51; 935/72
[58] Field of Search ............... 435/68, 70, 172.3, 226, 435/253, 227, 228, 240, 170; 935/1, 6, 11, 44, 51, 70, 71, 73

[56] References Cited
FOREIGN PATENT DOCUMENTS

A20095351 11/1983 European Pat. Off. .

OTHER PUBLICATIONS

Mutt et al., (1970), *Eur. J. Biochem.*, vol. 15, pp. 513–519.
Shine et al., (1980), *Nature*, vol. 285, pp. 456–461.
Rossi et al., (1982), *J. Biol. Chem.*, vol. 257, pp 9226–9229.
Suzuki et al., (1982), *Proc. Nat'l Acad. Sci., U.S.A.*, vol. 79, pp. 2475–2479.
Bradbury, A. et al., 1982, Nature, 298: 686, 301.
Husain and Tate, FEBS Letters, 152: 277–281, (1983).

Primary Examiner—Thomas G. Wiseman
Assistant Examiner—Stephanie Seidman
Attorney, Agent, or Firm—Finnegan, Henderson, Farabow, Garrett & Dunner

[57] ABSTRACT

Secretin, which cannot be prepared directly by genetic engineering because of its carboxylic acid carboxyl-terminus, can be obtained by preparing secretylglycine by genetic engineering and then obtaining secretin therefrom by enzymatic conversion of the terminal glycine radical. The gene for the secretylglycine is synthesized chemically from smaller single-stranded units which are linked enzymatically to give the complete gene, incorporated into a suitable vector and amplified therein, after which the peptide is isolated directly or as a fusion protein and, after cyanogen bromide cleavage, is converted enzymatically into secretin.

5 Claims, 2 Drawing Figures

```
5' AATTC ATG CAT TCT GAC GGT -
    G TAC GTA AGA CTG CCA -
  Eco RI   Ava III

ACC TTC ACT TCT GAA CTG
  TGG AAG TGA AGA CTT GAC
  Kpn I

TCT AGA CTG CGT GAC TCT
  AGA ACA GAC GCA CTG AGA
  Xba I

GCT CGA CTC CAG CGT CTG
  CGA GCT GAG GTC GCA GAC
       Xho I

CTG CAG GGT CTG GTT GGT
  GAC GTC CCA GAC CAA CCA
     Pst I

TAG TA
  ATC ATT CGA
     Hind III
```

FIG. 1

5' AATTC ATG CAT TCT GAC GGT -
      G TAC GTA AGA CTG CCA -
Eco RI   Ava III

ACC TTC ACT TCT GAA CTG
TGG AAG TGA AGA CTT GAC
Kpn I

TCT AGA CTG CGT GAC TCT
AGA ACA GAC GCA CTG AGA
Xba I

GCT CGA CTC AGC GTC TG
CGA GCT GAG GTC GCA GAC
Xho I

CTG CAG GGT CTG GTT GGT
GAC GTC CCA GAC CAA CCA
Pst I

TAG TA
ATC ATT CGA
Hind III

FIG. 2

```
                    Ia
        5'  AATTC ATG CAT TCT GAC GGT ACC -
        3'        G TAC GTA AGA CTG CCA TGG -
                  Ib

Ic
            TTC ACT TCT GAA CTG TCT AGA
            AAG TGA AGA CTT GAC AGA TCT

Id
                       Ie
            CTG CGT GAC TCT GCT CGA CTC
            GAC GCA CTG AGA CGA GCT GAC
                                 If

Ig
            CAG CGT CTG CTG CAG GGT CTC
            GTC GCA GAC GAC GTC CCA GAC
                                    Ih

5'  GTT GGT TAG TA
        3'  CAA CCA ATC ATT CGA
```

PREPARATION OF SECRETIN

German Patent Application No. P 33 27 007.4 (which has not previously been published) has proposed a process for the preparation of a polypeptide of the formula I $$Y-R-NH_2 \qquad (I)$$

in which Y is the methionine residue or a residue, bonded via methionine, of a bacterial protein and R denotes a peptide sequence of genetically codable amino acids, which comprises producing a polypeptide of the formula II $$Y-R-NH-CH_2-COOH \qquad (II)$$

by genetic engineering and converting the produce enzymatically into the polypeptide of the formula I. In a preferred embodiment of this process, a peptide of the formula II in which R contains no methionine residue is produced by genetic engineering and the radical Y is then split off by cyanogen bromide cleavage.

It has now been found that secretin can also be prepared by this process.

Secretin, a hormone from the duodenum, is a heptacosipeptide of the formula

H—His—Ser—Asp—Gly—Thr—Phe—Thr—Ser—Glu—Leu—
—Ser—Arg—Leu—Arg—Asp—Ser—Ala—Arg—Leu—Gln—
—Arg—Leu—Leu—Gln—Gly—Leu—Val—NH$_2$ (Eur. J. Biochem. 15, 1970, pages 513–519).

It stimulates bicarbonate secretion by the pancreas and inhibits gastrin-stimulated gastric acid secretion. For these reasons, secretin promises to be a good medicament for gastrointestinal disorders, such as, for example, for lesions in the gastrointestinal tract.

However, therapy with secretin has been frustrated because of the high production costs of isolated naturally occurring secretin, which occurs in only a very small amount in the mucosa of the small intestine. For this reason, numerous secretin syntheses have already been described which provide a relatively large amount of secretin but are unsatisfactory because of the large amount of effort and the high costs associated therewith. Secretin has thus been synthesized stepwise using the p-nitrophenyl ester method (J. Am. Chem. Soc. 89, 1967, pages 6,753–6,757) or the "Repetitive Excess Mixed Anhydride" (REMA) method (Helv. Chim. Acta 59, 1976, pages 1,112–1,126; and Int. J. Peptide Protein Res. 18, 1981, pages 276–283) or on a solid phase (Int. J. Peptide Protein Res. 9, 1977, pages 63–70). The use of segments for the synthesis of secretin requires coupling methods which are as far as possible free from racemization. It has thus already been possible to synthesize secretin using the azide method (J. Am. Chem. Soc. 90, 1968, pages 4,711–4,715) and the dicyclohexylcarbodiimide/N-hydroxysuccinimide method (Chem. Ber. 105, 1972, pages 2,508–2,514). Further variants of the DCC coupling consisted in the use of racemization-reducing and solubility-imparting additions of 1-hydroxybenzotriazole and 3-hydroxy-4-oxo-3,4-dihydro-1,2,3-benzotriazine (Chem. Ber. 107, 1974, pages 215–231; and Gut Hormones, Ed. S. R. Bloom, 1978, pages 165–168).

In contrast, the process according to the invention represents an efficient method of preparing secretin in high purity.

The preparation of deamido-secretin in *Escherichia coli* by genetic engineering is already known (M. Suzuki, S.-I. Sumi, A. Hasegawa, T. Nishizawa, K.-I. Miyoshi, S. Wakisaka, T. Miyake and F. Misoka, Proc. Natl. Acad. Sci. USA 79, 1982, pages 2,475–2,479). Here, the synthetic secretin gene was bonded at the N-terminal end via a methionine to the β-lactamase gene. After expression, the modified β-lactamase was isolated and the peptide was isolated from the protein by cyanogen bromide cleavage.

In contrast, according to the invention, secretylglycine is produced by genetic engineering and is converted enzymatically into secretin. Advantageous embodiments of this invention are illustrated in more detail below.

As is known, the genetic code is "degenerate", i.e. only two amino acids are coded for by a single nucleotide sequence, whilst the remaining 18 genetically codable amino acids, are allocated to 2 to 6 triplets. There is therefore an incalculable diversity of codon possibilities for the synthesis of the gene. The invention thus relates to a particularly advantageous DNA sequence, which is laid down in Scheme 1 (annex) and is also designated DNA sequence I below.

An "overlapping" DNA sequence, corresponding to the restriction endonuclease EcoRI is located on the 5' end of the coding strand, whilst the single-stranded, overlapping sequence corresponding to the restriction enzyme Hind III is located on the 3' end of the coding strand. These two different recognition sequences ensure insertion of the DNA in plasmids in the desired orientation.

The codon for the amino acid methionine is located on the 5' end of the coding strand between these recognition sequences and the codons for the amino acid sequence. At the end of this strand, the codon for glycine and, advantageously, 2 termination triplets follow the triplet coding for valine.

Within the structural gene, a number of singular recognition sequences for restriction endonucleases have been incorporated which, on the one hand, provide access to part sequences of the secretin and, on the other hand, allow mutuations to be performed. These cutting sites are inserted in the DNA sequence of Scheme 1.

The DNA sequence I can be built up from 8 oligonucleotides with different nucleotide lengths by first synthesizing these chemically and then linking them enzymatically via "sticky ends" of 6 nucleotides.

DNA sequence I has furthermore taken into consideration that, in the case of those amino acids to which several codons are to be allocated, these are not equivalent but, rather, show different preferences in the particular host cell, such as *E. coli*. Moreover, palindromic sequences have been reduced to a minimum.

The gene structure of DNA sequence I is thus easily accessible from relatively small units, facilitates subcloning of gene fragments into well-known vectors and allows expressions thereof in a high yield.

Scheme 2 shows the nucleotide sequence of Scheme 1, but the gene units Ia to Ih, which are used for synthesis of the gene, have been emphasized.

These oligonucleotide units can be prepared by known synthetic techniques (S. A. Narang, Tetrahedron 39, 1983, page 3; and S. J. Beaucage and M. H.

Caruthers, Tetrahedron Lett. 22, 1981, page 1,859). The phosphite method has been used, employing as protective groups on the heterocyclic radicals benzoyl for cytosine and adenine, as well as isobutyroyl for guanine, dimethoxytrityl on the 5'—OH group of the deoxyribose, and methyl as the ester protective group on the phosphorus. The phosphites were activated with tetrazole (J. L. Fourrey and D. J. Shire, Tetrahedron Lett. 1981, page 729). The reaction was carried out on silica gel, as a polymeric carrier, and in each case monomeric nucleoside phosphites were added. Working up was by dealkylation of the methyl ester groups on the phosphorus (G. W. Daub and E. E. van Tamelen, J. Amer. Chem. Soc. 99, 3,526 (1977)), detachment of the oligonucleotide from the carrier and removal of the amide protective guide with concentrated aqueous ammonia. The oligonucleotides were purified either by means of HPLC on reversed phase or ion exchange columns or by acrylamide gel electrophoresis (Chemical and Enzymatic Synthesis of Gene Fragments, Ed. H. G. Gassen and A. Lang, Verlag Chemie, Weinheim 1982, page 177).

The oligonucleotides thus obtained are then phosphorylated on the 5' end with polynucleotide-kinase and enzymatically linked with T-4-DNA-ligase in a known manner (V. Sgaramella and H. G. Khorana, J. Mol. Biol. 72, 427 (1972)).

The invention likewise relates to this synthetic gene thus obtained and to the units used for its synthesis.

Cloning of the resulting gene for secretylglycine in plasmids, such as pBR 322, was carried out by known methods (Molecular Cloning, T. Maniatis, E. F. Fritsch and J. Sambrook, Cold Spring Harbor, 1982, page 211). Besides the possibility of direct expression of the secretylglycine in E. coli, the structural gene, for example in the pBR 322, is ligated as a fusion peptide at the end of the β-galactosidase gene, into a plasmid which produces β-galactosidase. For this, two further oligonucleotides are required as linkers in order to insert the structural gene into the plasmid.

A gene is thereby formed which contains the nucleotide sequence for the 1,005 N-terminal amino acids of β-galactosidase and the nucleotide sequence for methionylsecretylglycine. E. coli serves as the host cell for transformation of the plasmid described above. A protein which contains the the amino acid sequence of β-galactosidase (1–1,005) N-terminally and the sequence for methionylsecretyl-glycine C-terminally is expressed. Cyanogen bromide cleavage releases secretyl-glycine from this protein.

The invention likewise relates to the hybrid plasmids containing the synthetic gene, the host organisms thus transformed, the methionyl-secretyl-glycine expressed and the corresponding fusion proteins as well as the secretylglycine prepared therefrom.

The chromatographic properties of secretylglycine are more hydrophilic than those of secretin. The biological activity of secretylglycine of about 800 KU/mg is significantly less than that of secretin. Stimulation of pancreatic secretion in dogs was used as a test of the biological action.

It was possible, with the aid of amide-forming enzymes (Nature 298, 1982, pages 686–688), to obtain fully active secretin with about 4,000 KU/mg of protein from the secretylglycine after another chromatographic purification.

In the following Examples, percentages are by weight (unless indicated otherwise).

EXAMPLE 1:

Synthesis of the oligonucleotides described in Scheme 2

The synthesis of the fully protected nucleotides was carried out according to the following scheme:

Commercially available (®)FRACTOSIL (Merck, Darmstadt) was converted into propylamino-silica gel by known methods (Chemical and Enzymatic Synthesis of Gene Fragments, Ed. H. G. Gassen and A. Lang, Verlag Chemie 1982, page 71). A 5'-0-dimethoxytrityl-nucleoside 3'-0-succinate was linked as an amide to the propylamino silica gel using dicyclohexylcarbodiimide (see above literature reference).

The oligonucleotides were prepared by the following cycle:

100 mg (2–4 μmol of nucleoside) of the polymer prepared above are treated successively in a sintered funnel as follows:

1. washing twice with nitromethane containing 1% of water;
2. leaving to stand, for two minutes in each case, three to five times in a saturated zinc bromide solution in nitromethane/1% water and subsequent filtration with suction;
3. washing twice with methanol;
4. washing twice with tetrahydrofuran;
5. washing twice with acetonitrile;
6. leaving to stand with 60–70 mg of nucleoside phosphite and 40 mg of tetrazole in 1 ml of anhydrous acetonitrile for five minutes and filtration with suction;
7. leaving to stand with a mixture of 20% strength acetic anhydrive in tetrahydrofuran/lutidine/dimethylaminopyridine (5:4:1/v,v,v) for two minutes and filtration with suction;
8. washing twice with tetrahydrofuran;
9. leaving to stand with a mixture of tetrahydrofuran/water/lutidine (2:1:2/v,v,v) for two minutes and filtration with suction;
10. leaving to stand with a mixture of 3% of iodine in tetrahydrofuran/water/collidine (1:4:5/v,v,v) for two minutes and filtration with suction;
11. washing twice with tetrahydrofuran;
12. washing twice with methanol;
13. return to 1.

The synthesis cycle is then repeated with the particular nucleoside phosphite until the chain is complete. The efficiency of each coupling step is measured spectroscopically by means of the absorption at 494 nm of the dimethoxytrityl cation, which is formed when the protective group is split off with the zinc bromide solution. When the synthesis is complete, the fully protected oligonucleotide is treated with 2,4,6-trimethylthiophenol/triethylamine (1:1/v,v) for one hour, the phosphoric acid methyl ester being dealkylated. The still partly protected nucleotide is then detached from the silica gel with saturated aqueous ammonia solution in the course of three hours. The ammoniacal solution is filtered and left to stand at room temperature for a further 50–60 hours in order to remove the remaining protective groups completely from the oligonucleotide.

The deblocked nucleotides are purified either by HPLC on reversed phase columns (eluting agent: 0.1M triethylammonium acetate in water against an acetonitrile gradient; Chemical and Enyzmatic Synthesis of Gene Fragments, Ed. H. G. Gassen and A. Lang, Verlag Chemie, Weinheim 1982, page 177) or by gel electrophoresis on 20% of acrylamide, 7M urea gels with 0.1M tris borate buffer, pH 8.3 (above literature reference, page 37).

The oligonucleotides Ia to Ih shown in Scheme 2 and the following nucleotides IIa and IIb were prepared by this process:

```
IIa: 5' AGCTTGACGCG
IIb: 3'     ACTGCGCTTAA
```

EXAMPLE 2:

Phosphorylation of the oligonucleotide blocks

The construction of the methionyl-secretylglycine gene as a duplex is represented in Scheme 2.

0.03 ml of a solution which is 10 mM in MgCl₂, 50 mM in tris-buffer, 0.2 mM in ATP and 20 mM in dithiothreitol (DTT) and contains 5 units (progress in Nucleic Acid Research 2, 1972, page 815) of T4-polynucleotide kinase is added to 3 μg of oligonucleotide. The course of the reaction is determined by chromatography on diethylaminoethyl (DEAE) paper or polyethyleneimine (PEI) cellulose. The resulting solution is further processed directly, without purification.

EXAMPLE 3:

Ligation of the nucleotide blocks Ia-h

In each case 500–800 pmol of 5'-phosphorylated Ib-Ig and 1.2 equivalents of 5—OH—Ia and —Ih are heated separately as Ia/b, Ic/d, Ie/f and Ig/h at 95° C. in water for two minutes and are slowly cooled to room temperature.

The samples are then all combined, lyophilized and taken up in 0.05 ml of 0.02M HEPES (2-[4-(hydroxyethyl)-1-piperazinyl]-ethanesulfonic acid) buffer) (ph 7.6). 200 units (J. Biol. Chem. 243, 1968, page 4,543) of T4-DNA-ligase are added. After incubation at 14° C. for 16 hours, the reaction is ended by heating the mixture to 80° C. The product is then isolated as a double strand with 102 base pairs (comparison by Hae III digestion of pBR 322) on a 10% polyacrylamide gel (without urea) and is purified.

Working-up: see Molecular Cloning, page 173

EXAMPLE 4:

Cloning of the methionyl-secretylglycine gene in pUC 8 pUC 8 (P. L. Biochemicals, GmbH) was cleaved with the restriction endonucleases Eco RI and Hind III under standard conditions (New England Biolabs, Inc., Beverley, MD, USA) and the large fragment was purified by agarose gel electrophoresis (1% of low-melting agarose: Bethesda Research Laboratories, Inc., Gaithersberg, MD, USA) in 0.1M tris-borate (2.5 mM EDTA). The large band was isolated by melting the agarose at 65° C. The product is extracted with phenol/chloroform (1:1,v/v). Ethanol is added to the aqueous phase. The precipitate is removed by centrifugation.

The methionyl-secretylgylcine gene (10 μg) synthesized in Example 3 is incubated with 20 μg of the Eco RI/Hind III fragment of pUC 8 in 0.02 ml of a 5 mM trisbuffer (pH 7.6, 10 mM in MgCl₂, 1 mM in ATP, 20 mM in DTT and 200 units of T4 DNA-ligase) at 14° C. for 12 hours.

The transformation in *E. coli* K 12 was carried out by known methods (Proc. Natl. Acad. Sci. USA 69, 1972, pages 2,110–2,114), and the transformants resistant to 25 μg/ml of ampicillin were isolated. Further analysis of selective transformants was carried out by treatment with restriction enzymes. Three clones were isolated which, after digestion with Eco RI and Hind III, received an insertion in the region of 102 base pairs (Bp). Cutting sites for Kpn I and Pst I were also present.

Sequencing according to A. M. Maxam and W. Gilbert (Methods of Enzymology 65, 1980, page 499) confirmed the synthesized sequence of the methionyl-secretylglycine gene.

EXAMPLE 5

Fusion of the methionyl-secretylglycine gene with the β-galactosidase gene of *E. coli*

For expression, the methionyl-secretylglycine gene described was cloned into the plasmid pWH 10. This plasmid vector is composed, according to customary processes (K. Itakura, T. Hirose, R. Crea, A. D. Riggs, H. L. Heyneker, F. Bolivar and H. W. Boyer, Science 1977, page 1,056), in one part of the *E. coli* plasmid pBR 322 and in the other part of the β-galactosidase gene plus a regulation unit. 10 μg of pBR 322 was digested with the restriction endonucleases Eco RI and Pvu II and separated on 5% polyacrylamide gel under standard conditions. The bands rendered visible with ethidium bromide (2,292 Bp) were cut out of the gel and subjected to electroelution. The gene for β-galactosidase and its regulation unit (3,185 Bb) were cut out of the transduction phage φ80 dlac by digestion with Eco RI and partial digestion by Pvu II. This fragment carries the lactase regulation region and the gene for the β-galactosidase of amino acid 1–1,005. This Lac-DNA fragment can be ligated with the DNA fragment of pBR 322. A plasmid with the regulation unit of the Lac-operon, the structural gene for the β-galactosidase of 1–1,005, the ampicillin-resistant gene of pBR 322 and its replication region result. The Lac-operon can be replaced as desired by other regulation regions, such as, for example, tac. This plasmid pWH 10 contains a singular Eco RI cutting point at amino acid 1,004 of the galactosidase, which is used as the cloning site. The structure gene of the methionyl-secretylglycine of 97 base pairs is provided at the 3' end with Hind III-Eco RI adaptor

```
IIa 5' AGCTTGACGCG
IIb 3'     ACTGCGCTTAA
     Hind III Eco RI
``` and is used for integration into the plasmid pWH 10. It is cut with Eco RI and the DNA piece with the gene for the methionyl-secretylglycine is then ligated in as described above.

The nucleotide sequence of the methionyl-secretylglycine gene is conceived such that the reading frame of the β-galactosidase passes continuously into the gene of the methionyl-secretylglycine. The genetic product from such a construction is a fusion of 1,005 amino-terminal amino acids of β-galactosidase (Proc. Natl. Acad. Sci. USA 74, 1977, page 1,507) with the C-terminal gene of the methionylsecretylglycine.

The orientation in which the methionyl-secretylglycine gene was inserted into the plasmid pWH 10 could be determined by means of restriction enzyme digestion.

EXAMPLE 6:

The *E coli* strain K 12 is used as the host cell for transformation of the plasmid pWH 10 described above.

The transformation is carried out by the customary methods of molecular biology (Molecular Cloning, page 211).

EXAMPLE 7:

Isolation of the β-galactosidase secretylglycine

The bacteria was grown to the desired optical density in a 30 liter fermenter under standard conditions in a complete medium or a synthetic medium with supplementation and are induced for two hours with a suitable inducer, for example isopropyl β-D-thiogalactoside. The cells are then killed with 0.1 mM benzylsulfonyl fluoride and 0.1% of cresol. After the cells have been centrifuged or filtered off, they are digested in an aqueous-acid medium at pH 3.0 with a FRENCH press or (®)DYNO mill (Willy Bachofen, Basle), and all the insoluble constituents are centrifuged off. The supernatant liquor is discarded. The residue is taken up in 7M guanidine hydrochloride and the mixture is centrifuged at 15,000 g. The supernatant liquor is decanted off and diluted with five times the amount of water. The mixture is brought to 0° C. and the resulting precipitate is centrifuged off. This is dissolved in 7M guanidine hydrochloride solution and chromatographed over (®)SEPHADEX G 200 in 7M guanidine hydrochloride. The fraction containing the β-galactosidase secretylglycine is diluted with five times the amount of water and the residue is centrifuged off.

Yield: 10 g

EXAMPLE 8

Secretylglycine

Secretylglycine was obtained by cyanogen bromide cleavage analogously to Proc. Natl. Acad. Sci. USA 79, 1982, pages 2,475-2,497 from the β-galactosidase secretylglycine obtained above and was then purified by chromatography on SP-SEPHADEX C-25 with ammonium acetate buffers (pH 6.8) of increasing molarity (from 0.05M to 0.1M). The ammonium acetate was removed by freeze-drying three times.

Yield: 50 mg (protein content according to amino acid analysis: 81%)

Amino acid analysis (hydrolysis: 24 hours in 6N HCl at 120° C.): Asp (2.01), Thr (2.03), Ser. (3.43), Glu (2.76), Gly (3.07), Ala (1.00), Val (0.89), Leu (5.57), Phe (1.12), His (0.89) and Arg (3.89).

Thin layer chromatography on a silica gel plate (60 F 254) in n-butanol/water/pyridine/glacial acetic acid =60:24:20:6% by volume; $R_f$=0.138 Biological action: about 800 KU/mg of pancreatic secretion in dogs.

EXAMPLE 9:

Secretin

The enyzme occuring in the neurosecretory granula fractions from hypothalami, which gives the corresponding peptide-amides from peptides lengthened C-terminally with glycine, was purified analogously to FEBS Letters 152, 1983, pages 277-279. These enzyme samples can be contaminated with enzymes which cleave after proline, which is no trouble in the case of secretin, since secretin contains no proline.

3 mg of secretylglycine are dissolved in 10 ml of 10 mM phosphate buffer (pH 7) and are incubated with a purified enzyme fraction in air and at 37° C., with stirring. After a reaction time of 5 hours, the solution is freeze-dried and purified by chromatography analogously to Example 8.

Yield: 1.2 mg (protein content according to amino acid analysis: 82%)

Amino acid analysis: hydrolysis: 24 hours in 6N HCl at 120° C.: Asp (1.99), Thr (1.91), Ser (3.52), Glu (2.99), Gly (1.99), Ala (1.01), Val (1.03), Leu (5.88), Phe (0.97), His (0.89) and Arg (3.91).

Thin layer chromatography on a silica gel plate (60 F 254) in n-butanol/water/pyridine/glacial acetic acid=60:24:20:6% by volume; $R_f$=0.189. The $R_f$ value is identical to that of synthetic secretin (Gut Hormones, Editor S. R. Bloom, 1978 pages 165-168). The biological action corresponds to about 4,000 KU/mg of protein and is comparable to that of synthetic secretin.

We claim:

1. A process for preparing a polypeptide of formula I $$Y-R-NH_2 \qquad (I)$$

in which Y is methionine or a radical of a bacterial protein bonded via methionine to R, and R is the amino acid sequence of secretin wherein said process comprises (1) producing by using recombinant DNA techniques a polypeptide of formula II $$Y-R-NH-CH_2-COOH \qquad (II)$$

in which Y and R are defined as above, and (2) enzymatically converting the polypeptide of formula II into the polypeptide of the formula I with an amidating enzyme.

2. The process as claimed in claim 1, wherein the radical Y is removed from the polypeptide of the formula I by cyanogen bromide cleavage.

3. The DNA sequence of the formula V

AA TTC ATG R GGT TAG TA
C TAC R CCA ATC ATT CGA in which R denotes the codons for the amino acid sequence of secretin.

4. A hybrid plasmid which contains a DNA sequence of the formula V as set forth in claim 3 inserted between an EcoRI and a HindIII restriction enzyme recognition site.

5. Host organisms containing a hybrid plasmid as claimed in claim 4.

* * * * *